US011246480B2

(12) United States Patent
Sagiv et al.

(10) Patent No.: US 11,246,480 B2
(45) Date of Patent: *Feb. 15, 2022

(54) PREVENTING FOG ON A MEDICAL DEVICE VIEWPORT

(71) Applicant: PLASMATICA LTD., Moshav Bnei Atarot (IL)

(72) Inventors: Adam Sagiv, Moshav Bnei Atarot (IL); Michael Maller, Eshar (IL); Amnon Lam, Kibutz Givat Oz (IL)

(73) Assignee: PLASMATICA LTD., Moshav Bnei Atarot (IL)

( * ) Notice: Subject to any disclaimer, the term of this patent is extended or adjusted under 35 U.S.C. 154(b) by 136 days.

This patent is subject to a terminal disclaimer.

(21) Appl. No.: 16/539,851

(22) Filed: Aug. 13, 2019

(65) Prior Publication Data

US 2019/0365215 A1    Dec. 5, 2019

Related U.S. Application Data

(63) Continuation-in-part of application No. 15/757,659, filed as application No. PCT/IL2016/050990 on Sep. 7, 2016, now Pat. No. 10,413,168.

(Continued)

(51) Int. Cl.
*A61B 1/12* (2006.01)
*G02B 1/18* (2015.01)
(Continued)

(52) U.S. Cl.
CPC ............. *A61B 1/127* (2013.01); *G02B 1/18* (2015.01); *G02B 27/0006* (2013.01);
(Continued)

(58) Field of Classification Search
CPC ......... A61B 1/127; A61B 1/253; A61B 1/126; A61B 1/00142; A61B 1/0011;
(Continued)

(56) References Cited

U.S. PATENT DOCUMENTS 3,925,178 A   12/1975   Gesser
4,055,378 A   10/1977   Feneberg
(Continued)

FOREIGN PATENT DOCUMENTS

CN    102512702    6/2012
CN    204618406    9/2015
(Continued)

OTHER PUBLICATIONS

International Search Report and Written Opinion from International Application No. PCT/IL2016/050990 dated Jan. 3, 2017.

*Primary Examiner* — Xiuyu Tai
(74) *Attorney, Agent, or Firm* — Dorsey & Whitney LLP

(57) ABSTRACT

Provided are methods of immunizing a viewport of a medical device against fogging before or during a medical procedure, and related apparatuses and devices. The methods comprise applying plasma to the viewport prior to use, thereby rendering a surface of the viewport highly hydrophilic. The methods eliminate or at least significantly reduce blur due to fogging.

8 Claims, 6 Drawing Sheets

Related U.S. Application Data

(60) Provisional application No. 62/215,061, filed on Sep. 7, 2015.

(51) Int. Cl.
  H05H 1/24 (2006.01)
  G02B 27/00 (2006.01)
  A61L 2/14 (2006.01)

(52) U.S. Cl.
  CPC .............. H05H 1/2406 (2013.01); *A61L 2/14* (2013.01); *A61L 2202/24* (2013.01); *H05H 2245/30* (2021.05)

(58) Field of Classification Search
  CPC ............ A61B 1/00137; A61B 1/00101; A61B 1/00135; G02B 1/18; G02B 27/0006; G02B 23/2476; H05H 1/2406; H05H 2245/30; A61L 2/14; A61L 2202/24
  See application file for complete search history.

(56) References Cited

U.S. PATENT DOCUMENTS

| | | | |
|---|---|---|---|
| 4,122,942 A | 10/1978 | Wolfson | |
| 4,143,949 A | 3/1979 | Chen | |
| 4,214,014 A | 7/1980 | Hofer | |
| 4,312,575 A | 1/1982 | Peyman | |
| 4,632,844 A | 12/1986 | Yanagihara | |
| 4,643,876 A | 2/1987 | Jacobs | |
| 6,855,329 B1 | 2/2005 | Shakesheff | |
| 7,931,584 B2 | 4/2011 | Akagi | |
| 8,047,215 B1 | 11/2011 | Sasaki | |
| 8,349,125 B2 | 1/2013 | Vane | |
| 8,409,077 B2 | 4/2013 | Orihara | |
| 8,663,625 B2 | 3/2014 | Stroock | |
| 9,072,443 B2 | 7/2015 | Hashido | |
| 9,248,207 B1 | 2/2016 | Heyoung | |
| 2002/0053353 A1 | 5/2002 | Kawata | |
| 2006/0252986 A1 | 11/2006 | Akagi | |
| 2008/0002146 A1 | 1/2008 | Stachowski | |
| 2013/0137928 A1 | 5/2013 | Karasawa | |
| 2014/0290700 A1* | 10/2014 | Langford | A61B 90/70 134/22.12 |
| 2014/0371528 A1 | 12/2014 | Yen et al. | |
| 2015/0005582 A1 | 1/2015 | Poll | |
| 2015/0209461 A1* | 7/2015 | Itarashiki | H05H 1/24 422/2 |

FOREIGN PATENT DOCUMENTS

| | | |
|---|---|---|
| EP | 1889562 | 2/2008 |
| JP | H0337030 A | 2/1991 |
| JP | H1043128 | 2/1998 |
| JP | 2002110397 | 4/2002 |
| JP | 2003207601 | 7/2003 |
| WO | 9504609 | 2/1995 |
| WO | 2006129472 | 12/2006 |

* cited by examiner

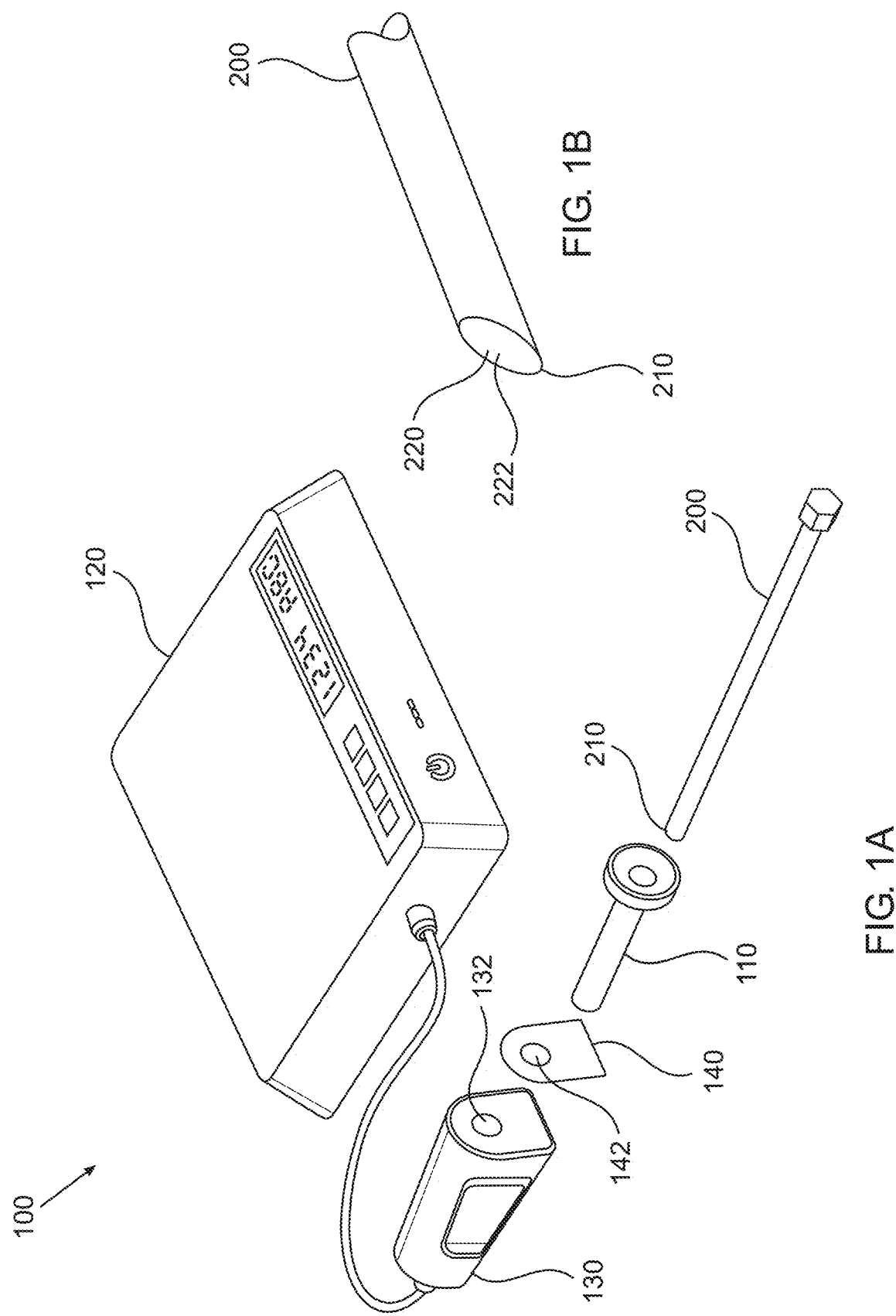

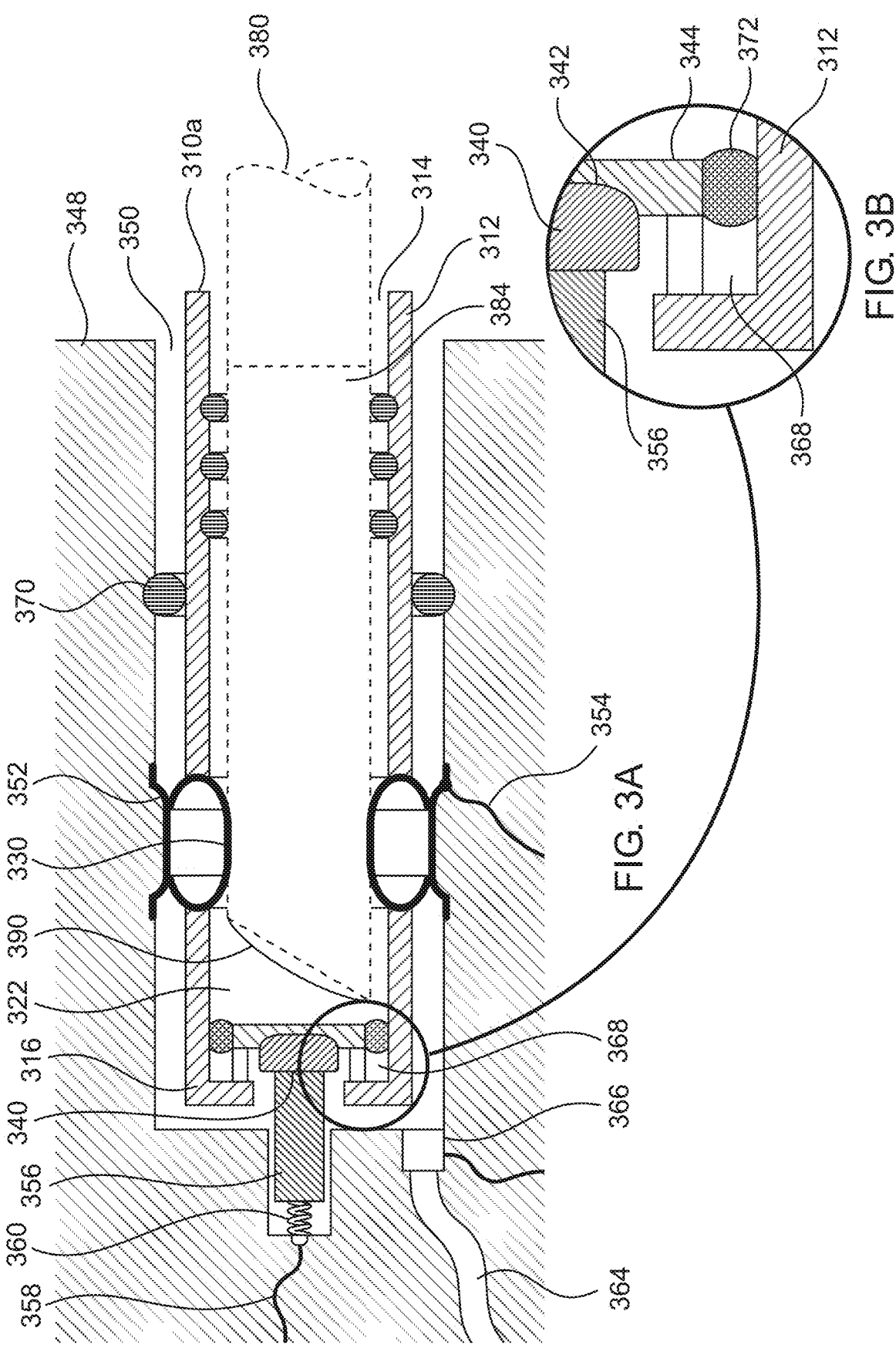

PREVENTING FOG ON A MEDICAL DEVICE VIEWPORT

CROSS-REFERENCE TO RELATED APPLICATIONS

This application is a continuation-in-part of U.S. application Ser. No. 15/757,659 filed on 6 Mar. 2018, which is a U.S. National Stage of PCT International Application No. PCT/IL2016/050990 filed on 7 Sep. 2016, which claims priority to U.S. Provisional Application No. 62/215,061 filed on 7 Sep. 2015. The disclosure of each of the foregoing applications is incorporated herein, in its entirety, by this reference.

FIELD OF THE INVENTION

The invention, in some embodiments, relates to the field of medical devices having a viewport such as endoscopes, and more particularly, but not exclusively, to methods and devices for immunizing medical devices against accumulation of fog on the viewport during a medical procedure.

BACKGROUND OF THE INVENTION

Endoscopes are widely used in medical procedures, particularly in minimally invasive surgical procedures. Here, an "endoscope" is intended to include any scope that has a distal end configured to be inserted into a patient's body, and a proximal end configured to remain outside the patient's body during the procedure. Typically, the distal end comprises a viewport such as a lens or a window or a bare end of an optical fiber or even a mirror (such as a dentist mirror for example). Through the viewport, the scope enables collecting an image of the surrounding of the viewport, e.g. using a light-sensitive device such as a CCD. The viewport may be aimed to collect light from in front of the device (namely from a region coinciding with the longitudinal axis of the device), or the viewport may be slanted in an angle relative to the longitudinal axis, or may be facing perpendicular to the longitudinal axis of the device (as is demonstrated for example in colonoscopies). The proximal end typically includes or is connected to a handle to be held by a medical practitioner, possibly including user interface components such as switches, navigating sticks, touch screens and touch pads.

Endoscopes include a vast range of scopes, for example bronchoscopes, colonoscopes, cystoscopes and laparoscopes. A laparoscope—as a specific example—comprises a rigid or relatively rigid rod or shaft having a viewport, possibly including an objective lens, at the distal end, and an eyepiece and/or an integrated visual display at the proximal end. The scope may also be connected to a remote visual display device or a video camera to record surgical procedures.

In a laparoscopic procedure, the patient's abdominal or pelvic cavity is accessed through one or two or more relatively small incisions (typically between about 3 mm and about 15 mm) and a laparoscope may be inserted through one of the incisions to allow the practitioner a view of the internal organs to be operated on. The abdomen is typically inflated with a gas through the use of an insufflator—carbon dioxide is usually used for insufflation—to distend the abdominal space by elevating the abdominal wall above the internal organs and thereby create a sufficient working and viewing space for the surgeon.

The local environment within a patient's abdominal space is generally humid and warm compared to the laparoscope which is being inserted. Consequently, the viewport of the laparoscope tends to blur, e.g. due to fog, that is to say due to condensation of vapor on the viewport, or, for example, due to accumulation of droplets, e.g. blood droplets originating from surgical activity during the procedure.

Some existing techniques used to clean the viewport of endoscopes require retreating the endoscope from the patient's body, rinsing the viewport or wiping it (e.g. with a cloth) and possibly drying the distal end and worming it, to reduce and slow down blur formation after introducing the endoscope back in the patient's body. Other existing techniques include rinsing the viewport inside the patient's body. U.S. Pat. No. 8,047,215 discloses a laparoscopic lens cleaner which is suitable for maintaining the lens of a laparoscope in a clean, dry condition during a laparoscopic surgical procedure. An embodiment of the laparoscopic lens cleaner includes an elongated cleaner sheath having a sheath interior, a fluid conduit provided in the cleaner sheath, a fluid discharge nozzle provided in the sheath interior and communicating with the fluid conduit, a gas conduit provided in the cleaner sheath and a gas discharge nozzle provided in the sheath interior and communicating with the gas conduit. US patent application 20150005582 discloses a method of defogging and cleaning a laparoscope. The method includes: inserting a laparoscope into a sheath; inserting the laparoscope and sheath into a body cavity; providing gas to a plurality of gas lumens within a wall of the sheath such that the gas flows through the gas lumens and over a lens of the laparoscope to defog the lens while the laparoscope is in the body cavity; and providing a fluid comprising a surface-active agent to a fluid lumen within the wall of the sheath such that the fluid flows through the fluid lumen and over the lens to clean the lens while the laparoscope is in the body cavity.

SUMMARY OF THE INVENTION

Aspects of the invention, in some embodiments thereof, relate to defogging—namely decreasing or preventing blur and fog—on a viewport of a medical device. More specifically, aspects of the invention, in some embodiments thereof, relate to methods and devices for immunizing the medical device against accumulation of fog on the viewport during a medical procedure.

As discussed above there are existing techniques for maintaining a viewport of a medical device clear during a medical procedure in which the medical device is used inside a patient's body. Such techniques involve active cleaning of the viewport, either by removing the medical device from the patient's body and cleaning the viewport with a cloth or by rinsing, or by rinsing the viewport (and possibly drying it using flow of gas) inside the patient's body, and are therefore less than optimal. Interruption of the medical procedure for cleaning results in lengthening the time of the procedure and may further cause various complications resulting from mind distraction of the medical practitioner or generally due to carrying out activity steps that are not medically required. Extracting the medical device from the patient's body for carrying out the cleaning is even worse, as such removal and then re-introduction of the device into the body may be a source of yet additional complications.

One reason that condensation of vapor on a viewport might cause blur, is that the condensed liquid—e.g. water, possibly mixed with body fluids—condenses into droplets which distort the light rays passing through the droplets, thereby ruining the optical quality of the viewport. In other words, each droplet might function as a lens, focusing or diverging or generally distorting the light rays passing therethrough in uncontrolled directions. The total effect of the multitude of droplets on the viewport is thus generating an optically rough surface, thereby preventing obtaining a sharp image from light passing the viewport (or reflecting therefrom).

There is thus provided, according to an aspect of some embodiments, a method of immunizing a viewport against fogging during use. According to some embodiments the view port may be a view port of a medical device such as an endoscope and the process of immunization may be provided prior to using the medical device in a medical procedure. The method comprises applying a plasma-generating electromagnetic field in a closed chamber that houses the viewport, in close vicinity to the viewport. The plasma treatment of the viewport is configured to increase hydrophilicity so as to achieve complete wetting of the viewport by water. Complete wetting is achieved by increasing the surface tension of the treated surface of the viewport to above the surface tension of water, namely above 0.072 N/m. Preferably, the surface tension of the viewport surface is elevated to above 0.08 N/m and even above 0.1 N/m for a limited time period following the plasma treatment as explained above. When the surface tension of the treated surface of the viewport is greater than the surface tension of water, water does not accumulate in droplets on the surface but rather wet the surface, having a contact angle of substantially 0 degrees. Thus, the method eliminates or at least significantly reduces blur due to fogging because condensation of moisture on the hydrophilic surface of the viewport results in a thin and even layer of fluid, thereby maintaining the optical quality of the viewport or at least limiting the degradation of the optical quality. Variations of fluid thickness on the viewport is reduced by the plasma treatment, and thereby variability in optical lengths associated with passing of light through the condensed fluid on the viewport is reduced as well.

The effects of plasma treatment on hydrophilicity of a treated surface are often temporary, so that hydrophilicity of a treated surface tends to decrease over time after the exposure to plasma ends. The method thus further comprises using the viewport (or the device in which the viewport is installed)—namely exposing the viewport to moisture—soon after applying the plasma. "Soon after" means within 24 hours, preferably within 6 hours and even more preferably using the viewport within less than an hour after applying the plasma thereto.

It is noted that according to the teachings herein, plasma is generated in a Dielectric Barrier Discharge (DBD) mode, to ensure uniformity of the plasma generating electric field in the vicinity of the view port, and hence to ensure the quality of the plasma treatment. The "quality" of the plasma treatment herein denotes the level of hydrophilicity attained, and the duration of time during which the electric field is activated to obtain that hydrophilicity. In other words, a high-quality plasma treatment achieves a relatively high level of hydrophilicity (e.g. obtaining a surface tension above that of water namely above 0.072 N/M on the treated surface) within a relatively short duration (e.g. of 5 minutes, or 1 minute or as short as 10 seconds or even as short as 5 seconds of activated electric field).

Plasma generation in a DBD mode may be effected, for example, by electrically isolating one of the electrodes used for applying the field. Such isolation may be realized by a dielectric layer that isolates the electrode from the gas in the region where plasma is generated; or a DBD mode may be effected, for example, by a dielectric layer that interrupts a line-of-sight between two electrodes between which the plasma-generating field is applied. For example, according to some embodiments, a dentist's mirror may be treated according to the teachings herein by placing the distal end of the device including the mirror with, e.g. a segment of the metallic handle, in a close chamber, electrically connecting a cathode to the metallic handle and applying a RF high voltage to an anode which is electrically isolated from the gaseous medium around the mirror. According to other exemplary embodiments, a view port made of a dielectric material such as glass or plastic and having no metallic parts in a vicinity thereof may be treated according to the teachings herein by being positioned in between two exposed electrodes used to apply the plasma-generating electric field, so that the view port itself is used as a dielectric barrier by interrupting the line of sight between the electrodes.

Generating plasma in a DBD mode as described herein allows positioning the electrodes at a relatively short distance from one another and at a short distance from the treated surface, and applying a relatively strong field while maintaining the field relatively uniform in close vicinity to the treated surface of the view port, thereby providing a high-quality plasma treatment to the treated surface ("relatively" here is used as compared to generating plasma not in a DBD mode).

According to an aspect of some embodiments there is further provided an apparatus for preparing an endoscope for an endoscopy procedure. The apparatus comprises a protecting shroud dimensioned to receive therein a distal end of the endoscope, the distal end comprising a viewport configured to enable collecting an image of the surrounding of the viewport there through. The apparatus further comprises a plasma generating field applicator, electrically associated with an electric power source and having a slot configured to receive therein the distal end of the endoscope shrouded within the protecting shroud. The plasma generating field applicator is configured to apply inside the slot an electric field suitable for plasma generation proximal the viewport. The protecting shroud is detachable from the distal end of the endoscope and from the plasma generating field applicator.

According to some embodiments the protecting shroud comprises at least one electrode and at least one shroud electric contact configured to electrically contact a corresponding applicator electric contact in the plasma generating field applicator when the protecting shroud is inserted into the slot. The at least one electrode is thereby configured to apply a plasma generating field within the protecting shroud upon receiving the electric power from the plasma generating field applicator.

According to an aspect of some embodiments there is provided an method of preparing an endoscope for an endoscopy procedure, comprising providing a protecting shroud dimensioned to receive therein a distal end of the endoscope, the distal end comprising a viewport configured to allow collecting an image of the surrounding of the viewport there through. The method further comprises providing a plasma generating field applicator, wherein the protecting shroud is detachable from the distal end and from the plasma generating field applicator. The plasma generating field applicator is electrically associated with an electric power source and has a slot configured to receive therein the distal end of the endoscope shrouded within the protecting shroud. The plasma generating field applicator is configured to apply electric power suitable for plasma generation within the protecting shroud. The method further comprises positioning the distal end of the endoscope shrouded within the protecting shroud in the slot of the plasma generating field applicator, and activating the power source to generate plasma within the protecting shroud, thereby plasma-treating the viewport of the distal end. According to some embodiments the method further comprises preventing, by the protecting shroud, contamination of the plasma generating field applicator with fluids dispersed on the distal end.

According to an aspect of some embodiments there is further provided a method of preparing an endoscope for an endoscopy procedure, the endoscope comprising a distal end comprising a view port. The view port is made of a dielectric material and is proximal to a metallic segment at the distal end of the endoscope. The method comprises placing the distal end of the endoscope in a plasma chamber that has at least an anode and a cathode wherein the cathode electrically contacts the metallic segment. A line-of-sight between the anode and the cathode is interrupted by a dielectric barrier, and the method further comprises applying a plasma-generating electromagnetic field between the anode and the cathode, thereby generating plasma in a DBD mode in a vicinity of the view port. According to some embodiments, the electric barrier electrically isolates the anode from gas in the vicinity of the view port.

According to some embodiments the viewport is transparent such as a viewport of a laparoscope. According to some embodiments the viewport is a mirror such as in a dentist's mirror. According to some embodiments the viewport is made of glass or quartz or plastic.

According to some embodiments, preparing an endoscope for an endoscopy procedure according to any of the procedures described herein, may include wetting the view port following the plasma treatment. Preferably, such wetting should be carried out prior to the endoscopy procedure or during the endoscopy procedure, prior to inserting the endoscope to the body of the patient. Such wetting may be carried out by dipping the view port in a liquid, preferably a polar liquid such as water or an aqueous solution. According to some embodiments such wetting may be carried out by wiping the view port with an article which is wetted by a desired liquid, e.g. by a wet cloth or a sponge or the like. Additionally or alternatively such wetting of the view port may be carried out by dispensing a controlled and accurate amount of liquid—e.g. an accurately measured droplet—on the view port. According to some such embodiments the amount of liquid may be calculated to be proportionate to the surface area of the view port, assuming a uniform liquid thickness. The resulting uniform liquid thickness may be smaller than about 100 microns (100 um) and even smaller than about 20 um, for example about 20 um or about 10 um, or about 5 um or about 1 um or about 0.5 um or about 0.2 um or about 0.1 um or even smaller than about 0.1 um. According to some embodiments the liquid may be water, or saline or an aqueous solution having a reduced surface tension (in air) such as a surfactant or a detergent. Such liquid may also comprise bio-compatible components or agents, e.g. hyaluronic acid.

Thus, according to some embodiments, a user may plasma-treat a view port of an endoscope according to the teachings herein, and soon after the plasma treatment, wet the view port as described above. Following wetting the view port, the user may proceed to insert the endoscope distal end to the patient's body in the course of the medical procedure being carried out.

This invention separately provides an apparatus which can be used for plasma treating a view port of a medical instrument such as an endoscope, for activating an external surface of the view port so as to obtain a surface tension of the external surface which is higher than the surface tension of water.

This invention separately provides a method of preparing a medical instrument having a view port, such as an endoscope, for a medical procedure, by plasma treating the view port for rendering the view port highly hydrophilic, thereby preventing blur due to fogging on the view port during use.

This invention separately provides a method of preparing a medical instrument for a medical procedure soon before the medical procedure or even during the medical procedure. The invention also provides an apparatus configured to provide plasma treatment to a medical instrument such as an endoscope soon before the medical procedure or even during the medical procedure in a clean and sterile environment.

Certain embodiments of the present invention may include some, all, or none of the above advantages. Further advantages may be readily apparent to those skilled in the art from the figures, descriptions, and claims included herein. Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures:

FIG. 1A schematically depicts an embodiment of an apparatus for preparing a medical device to a medical procedure, according to the teachings herein;

FIG. 1B schematically depicts a distal end of an endoscope, the distal end comprising a viewport suitable to be plasma-treated by the apparatus of FIG. 1A;

FIG. 3A schematically depicts a protecting shroud positioned inside a slot of a plasma applicator of the apparatus;

FIG. 3B schematically depicts a detail of the protecting shroud of FIG. 3A;

DETAILED DESCRIPTION OF SOME EMBODIMENTS

Figure 1C:
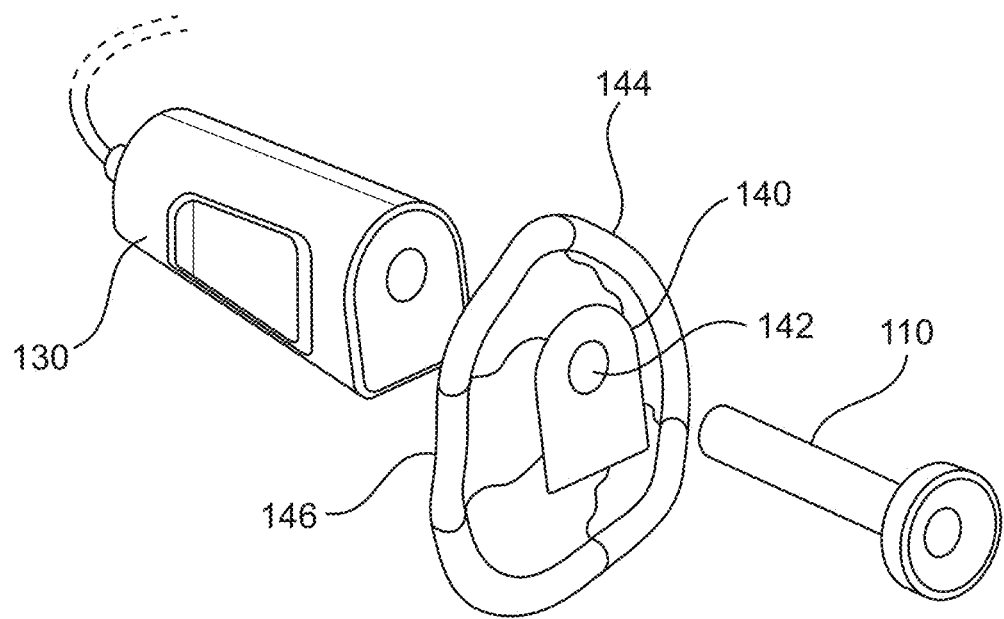
FIG. 1C schematically depicts a sterility screen of the apparatus of FIG. 1A, comprising a sterility sleeve for covering the plasma applicator of the apparatus of FIG. 1A, the sterility sleeve being rolled prior to use.

The principles, uses and implementations of the teachings herein may be better understood with reference to the accompanying description and figures. Upon perusal of the description and figures present herein, one skilled in the art is able to implement the teachings herein without undue effort or experimentation. In the figures, like reference numerals refer to like parts throughout.

FIG. 1A schematically depicts an apparatus 100, according to an aspect of some embodiments, for preparing a medical device 200 such as an endoscope, to a medical procedure. Medical device 200 comprises a distal end 210, schematically depicted also in FIG. 1B. Distal end 210 comprises a viewport 220 configured to enable collecting an image of the surroundings of the viewport. Viewport 220 may be in some embodiments a transparent sheet such as a window or a lens, of material such as glass or quartz, or plastic such as Perspex, thereby allowing light from the outside of the medical device 200 to be collected in the inside of medical device 200, e.g. by a light sensitive device (not shown here) such as a camera. According to some embodiments viewport 220 may be a mirror, reflecting light (rather than transferring light there through) towards a light collecting apparatus (not shown here) or a light sensitive device. Viewport 220 comprises a surface 222 which during a medical procedure may be exposed to moisture. Consequently, if not treated, e.g. immunized against fogging, surface 222 may thereby become covered with fog, such fog being the result of accumulation of droplets on the surface 222, e.g. (but not limited to) due to condensation of vapor.

Apparatus 100 comprises a protecting shroud 110 dimensioned to receive therein distal end 210 of the medical device 200. Apparatus 100 further comprises an operating unit 120 and a plasma applicator 130 (also referred to herein as a plasma generating field applicator) connected to the operating unit 120. Plasma applicator 130 comprises a slot 132 configured to receive therein distal end 210 of medical device 200, whereas distal end 210 is shrouded within protecting shroud 110. In other words, for use, distal end 210 of medical device 200 is inserted into protecting shroud 110, and protecting shroud 110, with distal end 210 being shrouded therein, is inserted into slot 132. According to some embodiments protecting shroud 110 is inserted into slot 132, and then distal end 210 is inserted and advanced into protecting shroud 110.

According to some embodiments apparatus 100 further comprises a sterility screen 140 having an opening 142. For use, protecting shroud 110 is inserted into slot 132 through opening 142 of sterility screen 140, as is further detailed and explained herein below. According to some embodiments protecting shroud 110 is a dispensable, disposable or replaceable part, being configured to be used during a single medical procedure carried out on a single patient. According to some embodiments, the protecting shroud functions as a sterility barrier between the endoscope which may be exposed to body fluids of the patient, and the plasma applicator, which may or may not be maintained sterile during use and after use. According to some embodiments sterility screen 140 facilitates maintaining plasma applicator 130 clear of body fluids originating in the endoscope during use and after use. According to some embodiments sterility screen 140 facilitates maintaining the endoscope sterile against contamination that may originate in plasma applicator 130.

Figure 1D:
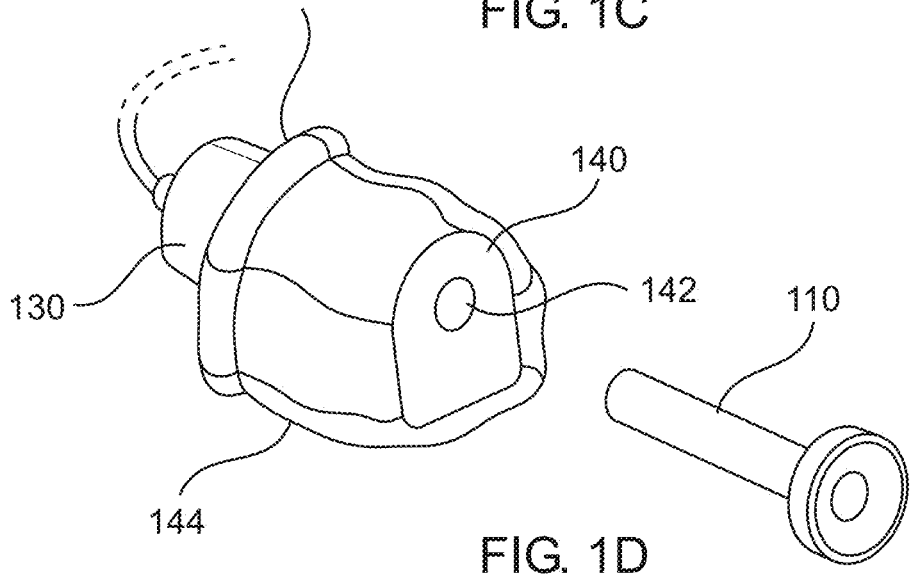
FIG. 1D schematically depicts the sterility screen of FIG. 1C, wherein the sterility sleeve is partially unrolled to cover the plasma applicator.
Figure 1E:
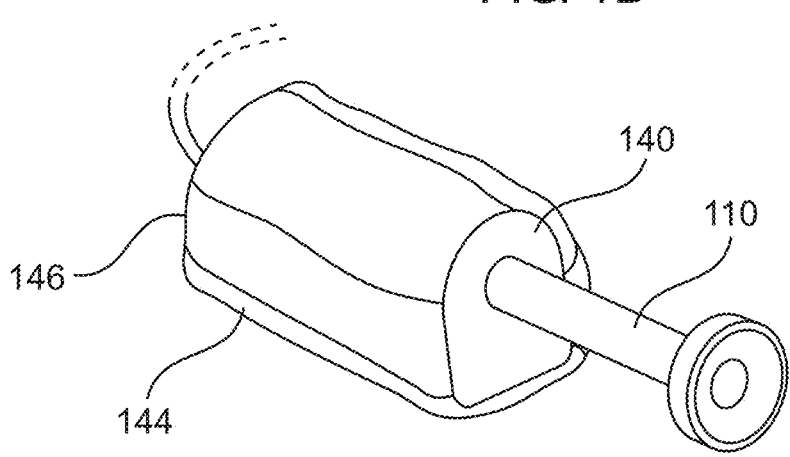
FIG. 1E schematically depicts the sterility screen of FIG. 1C, wherein the sterility sleeve is unrolled thereby covering the plasma applicator.

According to some embodiments sterility screen 140 is attached to a sterility sleeve 144, as depicted schematically in FIGS. 1C, 1D and 1E, the sterility sleeve extending between the sterility screen and a sleeve distal end 146. According to some embodiments sterility sleeve 144 may be soft like a sock. Prior to use, sterility sleeve 144 may be folded, as schematically depicted in FIG. 1C. For use, sterility sleeve 144 may be unfolded to encompass, envelop and cover plasma applicator 130 or a portion thereof by inserting the plasma applicator into the sterility sleeve through the sleeve distal end 146. During use, sterility sleeve 144 may be disposed around plasma applicator 130 so as to envelop and cover plasma applicator 130, so that insertion of protecting shroud 110 through opening 142 and into slot 132, and/or insertion of endoscope 200 into protecting shroud 110, may not contaminate plasma applicator 130. According to some embodiments the sterility sleeve may be substantially rigid, having a shape of e.g. a tube, being configured to house the protecting shroud therein. According to some embodiments sterility sleeve 144 comprises a double-sided sticky pad (not shown here) in a bottom portion thereof configured to stick on one side to plasma applicator 130 and to stick on another side to a desk or a table or another working platform, thereby attaching and stabilizing the plasma applicator to the working platform and facilitating inserting and extracting protecting shroud 110 (or endoscope 200) from plasma applicator 130. According to some embodiments, sterility screen 140 together with sterility sleeve 144, are attached to protecting shroud 110, so that insertion of protecting shroud 110 to the slot 132 and encapsulating plasma applicator 130 with sterility sleeve 144 are performed substantially together.

Plasma applicator 130 is electrically associated with an electric power source (not shown here). The power source may be optionally situated in operating unit 120. Plasma applicator 130 is further configured, when distal end 210, shrouded within protecting shroud 110, is positioned inside slot 132, and upon activation of the power source, to apply inside protecting shroud 110 inside slot 132 an electric field suitable for plasma generation proximal viewport 222.

According to some embodiments plasma applicator 130 may be fluidly associated with a gas pump and additionally or alternatively with a gas reservoir (neither one is shown here). The gas pump and the gas reservoir may be used to controllably evacuate, or to controllably flush with a preferred gas, respectively, a vicinity of the distal end of the endoscope, to facilitate plasma ignition, as is further detailed and explained below. According to some embodiments, a preferred gas may be argon or nitrogen. According to some embodiments, a gas pressure suitable for plasma ignition after evacuation may be below 0.1 Atm. According to some embodiments, the vicinity of the distal end of the endoscope may be pumped and evacuated and then flushed with a desired gas. According to some embodiments, the gas pump and/or the gas reservoir, as the case may be, may be optionally situated in the operating unit 120.

Operating unit 120 is configured to enable a user of apparatus 100 to operate and control the apparatus. Operating unit 120 may thus comprise command switches and controllers, such as physical or virtual switches, buttons and controllers. The control unit may further comprise indicators for providing a user with required data and information for operating the apparatus, such as indication LEDs, displays and possibly an operating software for providing a user with operating and command screens to allow a user operate and command the apparatus.

Figure 2:
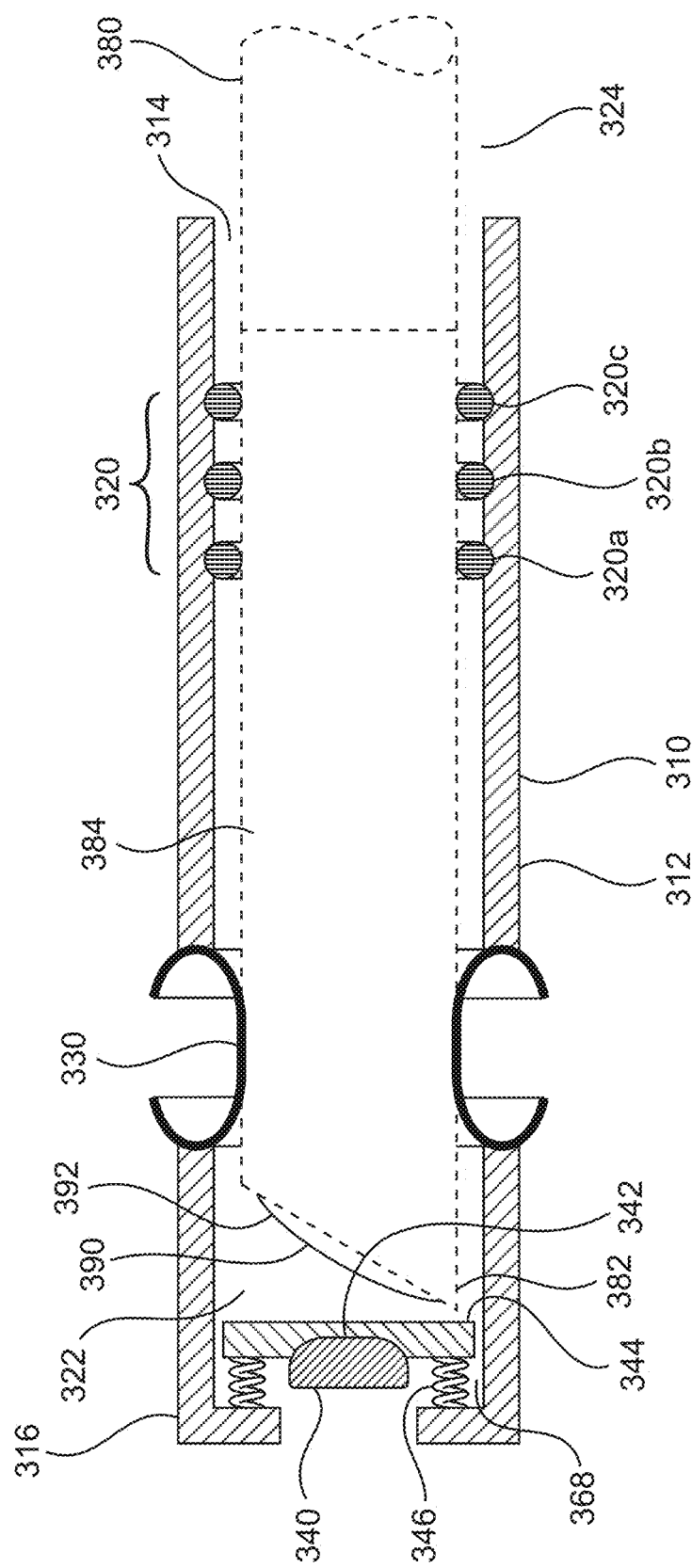
FIG. 2 schematically depicts an embodiment of a protecting shroud of an apparatus for preparing a medical device to a medical procedure according to the teachings herein, the protecting shroud shrouding an endoscope to-be plasma-treated.

FIG. 2 schematically depicts in a cross-sectional view, an embodiment of a protecting shroud 310 according to an aspect of some embodiments. Protecting shroud 310 is particularly suitable for use with an endoscope 380, depicted schematically inside protecting shroud 310 in dashed lines. Endoscope 380 comprises a distal end 382 and an electrically conducting surface—e.g. a metallic surface 384—at distal end 382, proximal a viewport 390. Viewport 390 further comprises an external surface 392, which may be subject to plasma treatment as described herein.

Protecting shroud 310 comprises a hollow cylinder 312 extending between a proximal opening 314 and a cylinder distal end 316. Protecting shroud 310 further comprises a vacuum seal 320 comprising three O-rings 320a, 320b and 320c, respectively. Vacuum seal 320 is adapted to fit an external dimension (e.g. an external diameter) of endoscope 380 so as to allow insertion of endoscope 380 into protecting shroud 310 using a slight force, e.g. by hand, as is known in the art. Accordingly, vacuum seal 320 is configured to hold a pressure difference (or gas concentration difference) between an inside 322 of protecting shroud 310 and an outside 324 of protecting shroud 310 when endoscope 380 is positioned inside protecting shroud 310. Vacuum seal 320 may also assist in mechanically stabilizing endoscope 380 inside protecting shroud 310, thereby assisting in preventing gas leakage between the inside 322 and the outside 324, and also assisting in plasma generation proximal viewport 390, as is further explained below.

Protecting shroud 310 further comprises a cathode 330 arranged on hollow cylinder 312 and configured to establish an electrical feedthrough between the outside 324 of protecting shroud 310 and the inside 322 thereof. Cathode 330 is flexible and electrically exposed on the inside 322 of protecting shroud 310 and on the outside thereof, thereby allowing insertion of endoscope 380 into protecting shroud 310 while forming an electric contact between cathode 330 and metallic surface 384. Protecting shroud 310 further comprises an anode 340 arranged proximal to cylinder distal end 316. Anode 340 may be shaped as a metallic block having for example a circular smooth surface 342 facing the inside 322. According to some embodiments the surface 342 may be curved. According to some embodiments (not shown here) anode 340 may be shaped as a pointed tip pointing towards the inside 322. According to some embodiments anode 340 may be shaped as a ring. Anode 340 is mounted on a disk 344 made of a dielectric material, so that disk 344 forms a dielectric barrier between anode 340 and cathode 330 and metallic surface 384 of the endoscope (which is on a same potential as the cathode). In other words, disk 344 is configured to ensure plasma generation in a Dielectric Barrier Discharge (DBD) mode of operation, by interrupting a line-of-sight between the anode 340 and cathode 330 and metallic surface 384 of the endoscope, thereby forming said dielectric barrier. In a DBD mode, plasma may be generated more uniformly over the available space in the vicinity of the view port, whereas arcing or other types of specific and narrow electric transportation trajectories between the anode and the cathode are prevented.

It is noted that the thickness of the dielectric barrier has a strong effect on the uniformity of the plasma generating electric field in the vicinity of the view port, and hence on the quality of the plasma treatment. The "quality" of the plasma treatment herein denotes the level of hydrophilicity attained, and the duration of time during which the electric filed is activated to obtain that hydrophilicity. In other words, a high-quality plasma treatment achieves a relatively high level of hydrophilicity (e.g. obtaining a surface tension above that of water namely above 0.072 N/M on the treated surface) within a relatively short duration (e.g. of 5 minutes, or 1 minute or as short as 10 second or even as short as 5 second of activated electric field). The thickness of the dielectric barrier should generally be as low as possible to facilitate plasma ignition, yet it should be large enough to prevent breakdown and arcing. Exemplary thickness of a dielectric material such as PET or polycarbonate in embodiments described herein may be in the range of about 0.3 mm to about 3 mm for RF electric field at frequencies in the MHz range (e.g. about 2 MHz).

According to some embodiments anode 340 is configured to displace flexibly relative to hollow cylinder 312, to facilitate a reliable electrical contact between anode 340 and a feeding contactor as is explained further below. According to some embodiments disc 344 may be supported by springs 346 relative to the cylinder 312.

In operation a plasma generating electric power is supplied between anode 340 and cathode 330 and consequently a plasma generating electric field in a DBD mode is generated between anode 340 and metallic surface 384 which is in contact with cathode 330. The plasma generating electric field generates plasma in the space between anode 340 and cathode 330 and particularly in the vicinity of viewport 390 and adjacent external surface 392.

FIG. 3A schematically depicts a portion of an embodiment of a plasma applicator 348 suitable for use with protecting shroud 310a (protecting shroud 310a is slightly different from protecting shroud 310 of FIG. 2, as is detailed below). Plasma applicator 348 comprises a slot 350 configured for receiving therein protecting shroud 310a (wherein endoscope 380 is shrouded within protecting shroud 310a). Plasma applicator 348 further comprises a cathode contactor 352 configured to contact cathode 330 when protecting shroud 310a is inside slot 350. An electric conductor 354 such as an electric wire, electrically associated with cathode contactor 352, may be used to supply electric power generated by a power source (not shown here) to cathode contactor 352 and to cathode 330. Plasma applicator 348 further comprises an anode contactor 356 configured to contact anode 340 when protecting shroud 310a is inside slot 350. An electric conductor 358 such as an electric wire, electrically associated with anode contactor 356 may be used to supply electric power generated by the power source to anode 340. Anode contactor 356 may be supported flexibly, e.g. by a spring 360, to facilitate a reliable electric contact between anode contactor 356 and anode 340 when protecting shroud 310a is inserted to the slot.

It is noted that characteristics of the electric field that could generate plasma in a gas may depend strongly on characteristics of the gas itself, in addition to the electrodes geometry involved (such as shape and configuration of electrodes used for the application of the electric field, distance between the electrodes etc.). Generally, the higher the pressure of the gas, the higher the electric field should be to ignite plasma in the gas. Also, some gases ignite at lower fields than others. For example, plasma may be ignited in helium gas at atmospheric pressure and using an RF field (in a frequency between 1 MHz and 15 MHz) of about 7 KV over a distance of 1 cm between electrodes, and at a voltage of about 200V if the gas is at a pressure of 0.8 KPa. With a similar configuration of electrodes and at similar field frequencies, plasma may be ignited in air at a voltage of about 20 KV in atmospheric pressure and at a voltage of about 800V in 0.8 KPa.

Thus, according to some embodiments, plasma applicator 348 is configured to stream gas from a gas reservoir (not shown here) to slot 350, or to pump air from slot 350, to generate a low-pressure atmosphere in the space between the electrodes 330 and 340, to facilitate plasma ignition. Thus, according to some embodiments, plasma applicator 348 is connected to a hose 364 fluidly associating a gas reservoir (not shown here) containing a gas suitable for plasma generation therein such as helium or argon or nitrogen, with slot 350. A valve 366 controlled by a control unit (not shown here) operable by a user, may be used to schedule and regulate the flow of gas into slot 350. During operation, according to some embodiments, after introducing protecting shroud 310a with endoscope 380 therein into slot 350, valve 366 may be opened to allow gas flow into the slot. Protecting shroud 310a may be penetrable to gas flow through openings 368 between hollow cylinder 312 and disc 344, enabling the gas to flow into protecting shroud 310a and towards viewport 390. Excess of gas flowing into slot 350 may freely escape through the gap in slot 350 between protecting shroud 310a and plasma applicator 348 (the gap being not sealed). Following a suitable time period of gas flow (e.g. 5 seconds or 10 second or 30 second or even 1 minute) the electric power source may be activated to supply power to anode 340 and cathode 330 to generate a plasma generating electric field near viewport 390. According to some embodiments the gas reservoir may be portable and suitable for a single time use.

According to some embodiments, hose 364 may be used to pump gas (air) from protecting shroud 310a and particularly from the space near viewport 390, to facilitate plasma ignition. Air may be sucked from the vicinity of viewport 390 through openings 368 towards slot 350 and into hose 364. A vacuum seal 370 enables generating vacuum near viewport 390 by withholding a pressure difference between a region near cylinder end 316 and a region near opening 314 of protecting shroud 310a. According to some embodiments air may be pumped through hose 364 by a vacuum pump (not shown here), fluidly associated with hose 364. According to some embodiments hose 364 may be fluidly associated to a pumped container (not shown) which is continuously pumped, e.g. by a small vacuum pump. Fluid association is provided through hose 364, the hose being in constant fluid communication with the container thereby being also continuously pumped. Opening valve 366 may result in pumping slot 350 and particularly the space near viewport 390 by the vacuum pump or by the pumped container, depending on the particularities of the embodiment. The volume of the pumped region in fluidly connected parts of slot 350 and of protecting shroud 310a may be, according to some embodiments, smaller than 10 cc, and a pumped container and hose of e.g. about 1000 cc (1 liter) may suffice to establish a suitable vacuum level between e.g. about 0.1 atm and about 0.01 atm within less than about 5 or less than about 10 seconds, which may be sufficient for plasma excitation for about 30 seconds or even about 1 minute to satisfactorily plasma-treat external surface 392.

According to some embodiments, depicted in detailed in FIG. 3B, protecting shroud 310a further comprises a sterility filter 372 positioned in openings 368 for maintaining a sterility barrier between protecting shroud 310a and plasma applicator 348. By maintaining a sterility barrier it is meant that microbial organisms may not penetrate sterility filter 372, wherein microbial organisms may include any form of prokaryotic cells or eukaryotic cells, including fungi and bacteria. The sterility filter is disposed according to some embodiments across cylinder end 316 in openings 368, so that gas flowing from plasma applicator 348 into protecting shroud 310a enters the protecting shroud sterile, and/or gas flowing from the inside 322 of protecting shroud 310a into plasma applicator 348 enters the plasma applicator sterile. Thus, the sterility filter 372 prevents transfer of contamination from the plasma applicator (e.g. from surroundings of slot 350) onto endoscope 380, and/or prevents transfer of contamination from endoscope 380 onto the plasma applicator. Additionally or alternatively, a sterility filter may be positioned in the plasma applicator, or for example in hose 364.

Figure 3C:
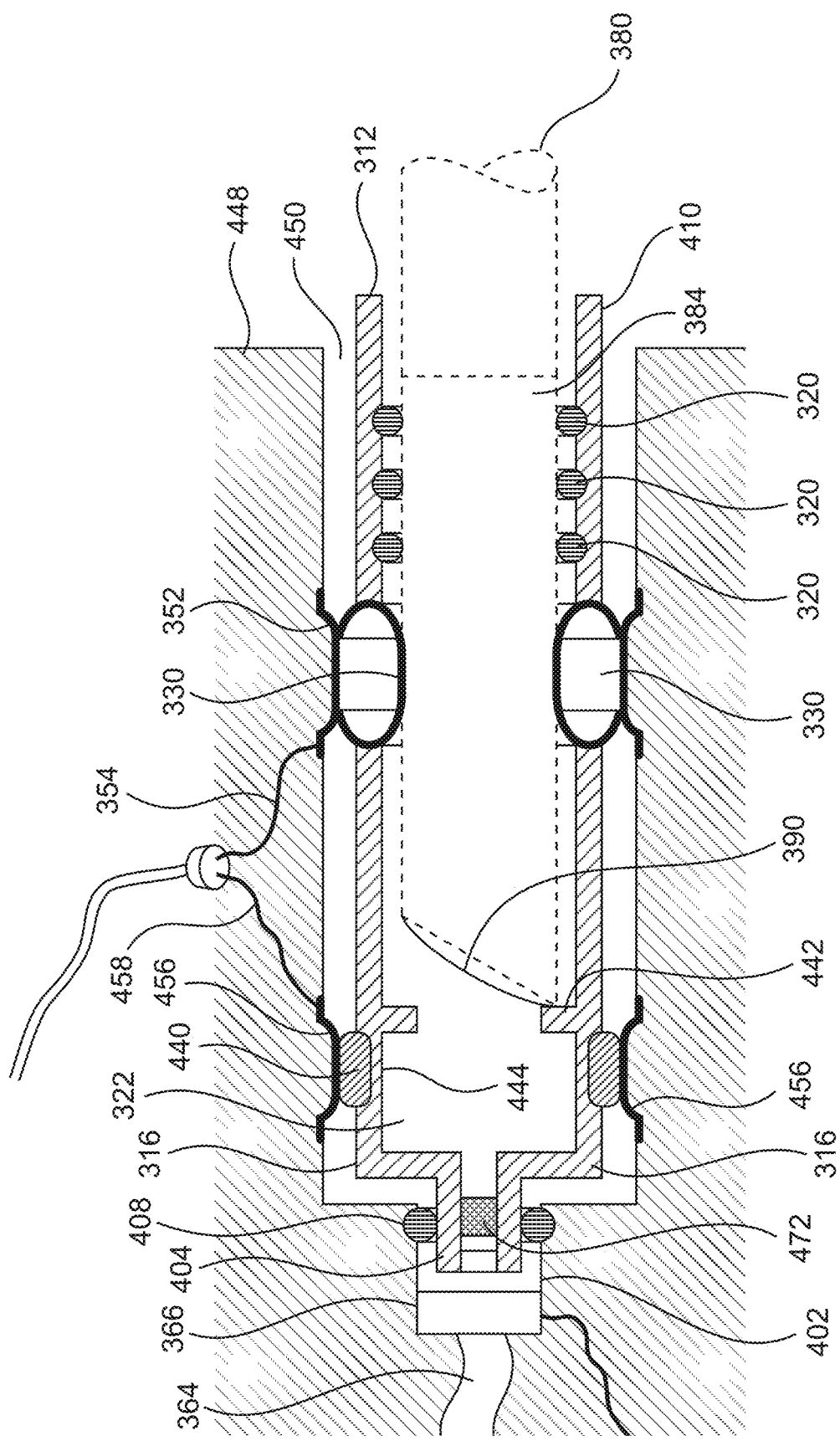
FIG. 3C schematically depicts another embodiments of a protecting shroud and a generating field applicator for preparing a medical device to a medical procedure according to the teachings herein, and FIG. 4 schematically depicts yet another embodiment of a protecting shroud of an apparatus for preparing a medical device to a medical procedure according to the teachings herein.

FIG. 3C schematically depicts a plasma applicator 448 and a corresponding protecting shroud 410 according to some exemplary embodiments. Plasma applicator 448 is different from plasma applicator 348 in comprising an applicator gas port 402 fluidly associated with hose 364, and protecting shroud 410 comprises a shroud gas port 404 configured to fluidly connect to the applicator gas port 402. Fluid connectivity between the inside 322 of the protecting shroud and the outside 324 of protecting shroud 410—e.g. the space of slot 450 of the plasma applicator—is prevented by a vacuum seal 408, e.g. an O-ring. Thus, when the protecting shroud 410 is inserted into the plasma applicator 448, the shroud gas port 404 fluidly connects to the applicator gas port 402 thereby establishing fluid connectivity of hose 364 to the inside 322 of the protecting shroud. Consequently, a plasma-ignition facilitating gas (such as helium or argon) may be driven directly into the protecting shroud through hose 364, and additionally or alternatively, gas, and particularly air, may be pumped from the protecting shroud through hose 364. Fluid connectivity between the slot 450 and the inside 322 of the protecting shroud is thus prevented. A sterility filter 472 is positioned inside shroud gas port 404, for maintaining a sterility barrier between the inside 322 of protecting shroud 410 and plasma applicator 448. As explained above regrading sterility filter 372 in FIG. 3B, gas flowing from plasma applicator 448 into the inside 322 of protecting shroud 410 enters the protecting shroud sterile, and/or gas flowing from the inside 322 of protecting shroud 410 into plasma applicator 448 enters the plasma applicator sterile. Thus, the sterility filter 472 prevents transfer of contamination from the plasma applicator (e.g. from surroundings of slot 450) onto endoscope 380, and/or prevents transfer of contamination from endoscope 380 onto the plasma applicator.

Protecting shroud 410 is further different form protecting shroud 310 in having a ring anode 440 shaped as a ring on an external circumference of hollow cylinder 312 near distal cylinder end 316 (instead of anode 340 in protecting shroud 310). Hence hollow cylinder 312, being made of a dielectric material, functions as a dielectric barrier 444 between anode 440 and cathode 330 and metallic surface 384 of the endoscope, so that plasma is generated in protecting shroud 410 in a DBD mode of operation as described above regarding protecting shroud 310. According to some embodiments protecting shroud 410 comprises a stopper 442 inside hollow cylinder 412. Stopper 442 is configured to limit advancement of endoscope 380 into protecting shroud 410, so that a pre-determined, desired gap is established between anode 440 and metallic surface 384 of the endoscope, thereby ensuring plasma generation at a known field (the field being determined by the voltage supplied between the cathode and the anode and the said gap). Stopper 442 may further be employed as a dielectric barrier on the line of sight between the anode and the cathode, thereby assisting in focusing plasma towards the view port 390.

When protecting shroud 410 is inserted into a slot 450 of plasma applicator 448, an anode contactor 456 of plasma applicator 448 contacts ring anode 440. Anode contactor 456 is electrically associated with an electric conductor 458 which is configured to connect to a power supply (not shown here) to enable providing to ring anode 440 a plasma generating electric field as described above. It is noted that cathode 330 is of protecting shroud 410 is electrically associated with cathode contactor 352 when protecting shroud 410 is inserted into a slot 450 as described above. Thus, upon activation, a suitably connected power supply may provide a plasma generating electric field (in a DBD mode) between ring anode 440 and the metallic surface 384 of endoscope 380 to generated plasma in the vicinity of view port 390.

Figure 4:
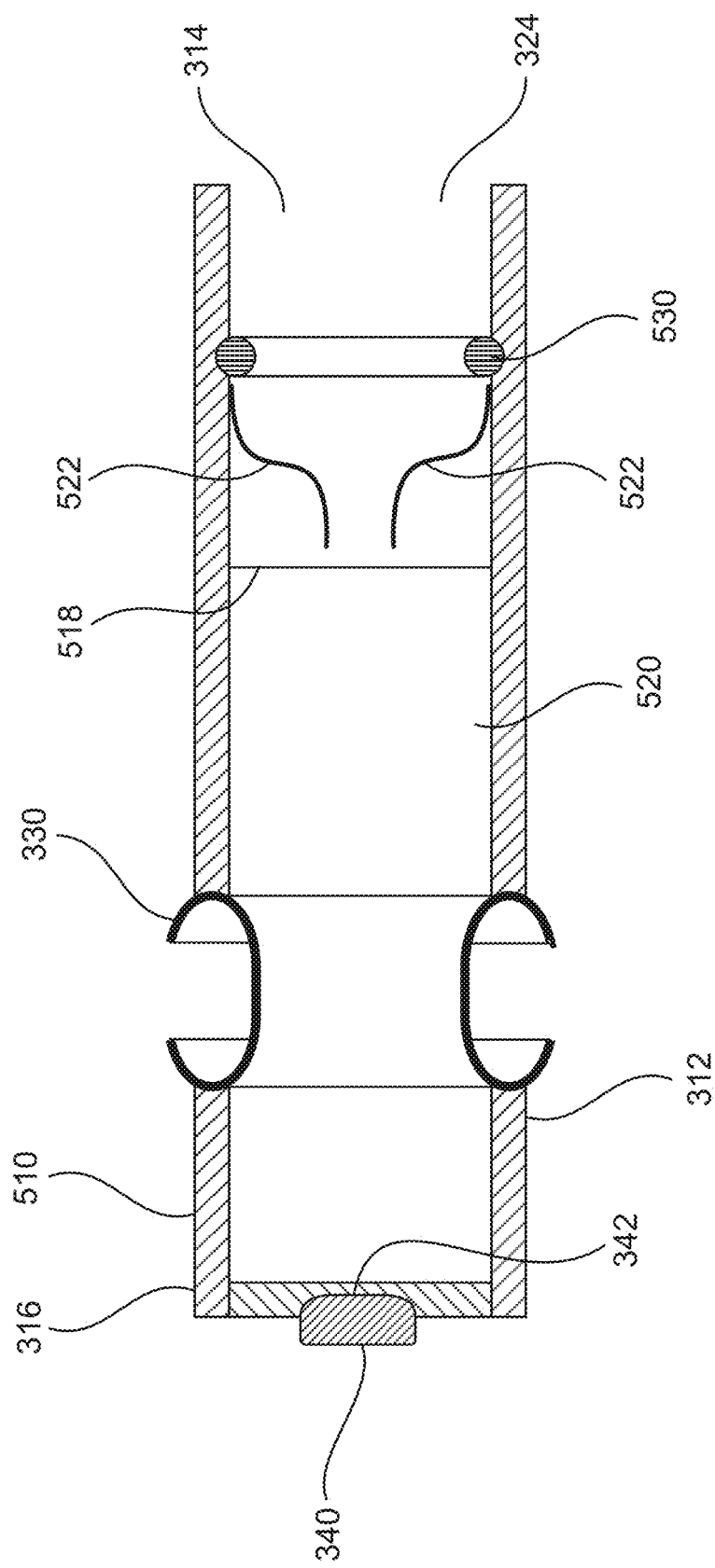

FIG. 4 schematically depicts a protecting shroud 510 according to an aspect of some embodiments. Protecting shroud 510 is configured to enable facilitated plasma ignition, without pumping the space around the endoscope as described in the embodiments above nor without streaming gas into that space. In other words, protecting shroud enables providing plasma treatment to a view port of an endoscope according to the teachings herein, using a plasma applicator that is not connected neither to a gas reservoir nor to a gas pump. Accordingly, the protecting shroud does not have a gas port such as gas port 402, and is not connected to a hose such as hose 364.

Protecting shroud 510 comprises hollow cylinder 312 extending between opening 314 and cylinder end 316. Protecting shroud 510 is different from protecting shroud 310 in that hollow cylinder 312 is blind and sealed near cylinder end 316, thereby substantially preventing permeation or penetration of gas molecules through cylinder end 316. Protecting shroud 510 is further different from protecting shroud 310 in having a leakage seal 530 inside hollow cylinder 312, and a hermetic screen 518 in hollow cylinder 312 situated between leakage seal 530 and cylinder end 316. Hermetic screen 518 is configured to be impermeable to gas molecules, thereby defining a closed space 520, closed between hermetic screen 518 and cylinder end 316. Closed space 520 inside protecting shroud 510 is thus airtight, namely maintained sealed from the outside 324 of protecting shroud 510. Closed space 520 contains a gas suitable for plasma ignition, e.g. Argon, at a gas pressure of about 1 atmosphere, so that there is, at most, only minor pressure gradients over the hermetic screen.

Hermetic screen 518 is breakable, being thereby configured to break (tear down) upon insertion of an endoscope such as endoscope 380 into protecting shroud 510. According to some embodiments, protecting shroud 510 further comprises one or more tearing needles 522 attached flexibly to hollow cylinder 312 near hermetic screen 518 outside of closed space 520. Tearing needles 522 are configured to lean flexibly towards hermetic screen 518 and to tear the hermetic screen when pushed by an object inserted into the protecting shroud. Thus, for use, the endoscope may be inserted into protecting shroud 510 and affecting tearing down of hermetic screen 518 by pushing tearing needles 522 towards hermetic screen 518. The endoscope may be further advanced until the viewport is between cathode 330 and anode 340. It is noted that during insertion, the endoscope is first advanced through leakage seal 530, then hermetic screen 518 is broken and then the endoscope is further advanced to be positioned in place. Once hermetic screen 518 is broken, the gas inside space 520 is prevented from freely flowing towards opening 324 by a sealing formed between leakage seal 530 and the endoscope. During further advancement of the endoscope into the protecting shroud, the free volume of space 520 for the gas reduces, yet pressure build up in the region of closed space 520 is prevented, due to gas escape under a pressure difference across leakage seal 530. As a result, when endoscope 380 is fully inserted into protecting shroud 510, closed space 520 and particularly the space proximal the viewport, between anode 340 and cathode 330, comprises substantially the gas that was contained in the space 520 before the tear-up of hermetic screen 518, at approximately atmospheric pressure, thereby facilitating plasma ignition therein. According to some embodiments hermetic screen 518 may be made of Mylar or metalized Mylar or Kapton or metalized Kapton and the like.

There is thus provided according to an aspect of the invention an apparatus (100 in FIG. 1A) for preparing an endoscope ((200 in FIG. 1, 380 in FIGS. 2, 3A and 3C) for an endoscopy procedure. The apparatus comprises a protecting shroud (110 in FIG. 1A, 310, 310a in FIGS. 2 and 3A, 410 in FIG. 3C, 510 in FIG. 4) dimensioned to receive therein a distal end (210, 382) of the endoscope. The distal end comprises a view port (220, 390) configured to enable collecting an image of the surrounding of the view port there through.

The apparatus further comprises a plasma generating field applicator (130, 348, 448), electrically associated with an electric power source. The plasma generating field applicator has a slot (132, 350, 450) configured to receive therein the distal end of the endoscope shrouded within the protecting shroud. The plasma generating field applicator is configured to apply electric power suitable for plasma generation within the protecting shroud. The protecting shroud is detachable from the distal end of the endoscope and from the plasma generating field applicator.

According to some embodiments the view port of the endoscope may be transparent or may be a mirror.

According to some embodiments the apparatus further comprises a sterility sleeve (144) extending between a first end (146) and a second end (140), configured to encapsulate the plasma generating field applicator, having on the first end a first opening configured to enable inserting the plasma generating field applicator into the sterility sleeve, and on second end a second opening (142) configured to enable inserting the endoscope into the plasma generating field applicator. According to some embodiments the sterility sleeve is soft and according to some embodiments the sterility sleeve is rigid. The sterility sleeve is detached from the plasma generating field applicator. According to some embodiments the sterility sleeve is attached to the protecting shroud, and according to some embodiments the sterility sleeve is detached from the protecting shroud.

According to some embodiments the protecting shroud comprises at least one electrode (340, 440) and a first shroud electric contact (340, 440) electrically connected to the electrode. The first shroud electric contact is configured to electrically contact a corresponding first applicator electric contact (356, 456) in the plasma generating field applicator when the protecting shroud is inserted into the slot (350,

450). The at least one electrode is thereby configured to apply a plasma generating field inside (322) the protecting shroud upon receiving the electric power from the plasma generating field applicator.

According to some embodiments the protecting shroud further comprises a second shroud electric contact (330), configured to contact the endoscope when the distal end of the endoscope is received within the protecting shroud. The second shroud electric contact is configured to electrically contact a second applicator electric contact (352) when the protecting shroud is inserted into the slot (350, 450).

According to some embodiments the protecting shroud comprises a hollow, substantially rigid tube (312, 412) extending between an opening (314) configured to receive the distal end of the endoscope, and a distal end (316) of the protecting shroud. According to some embodiments the hollow tube is a hollow cylinder (312, 412).

According to some embodiments the protecting shroud further comprises a seal (320, 530) positioned between the opening and the distal end along an inner circumference of the hollow tube, being dimensioned to encircle the endoscope (380), being thereby configured to sealingly contact the endoscope when the endoscope is received inside the hollow tube. According to some embodiments the seal comprises an O-ring.

According to some embodiments the plasma generating field applicator (348, 448) is connected to a hose (364). The hose is controllably fluidly connected to the slot (350, 450). According to some embodiments the plasma generating field applicator (348, 448) comprises a controlled valve (366), controllably fluidly connecting the hose (364) with the slot (350, 450). According to some embodiments the plasma generating field applicator (348) comprises an applicator gas port (402) fluidly connected with the hose, and the protecting shroud (410) comprises a shroud gas port (404). The shroud gas port is configured to sealingly connect with the applicator gas port for fluidly connecting the hose with an inside (322) of the protecting shroud. The sealed connection between the shroud gas port and the applicator gas port prevents, e.g. by seal 408, flow communication between the inside (322) of the protecting shroud (fluidly associated with hose 364) and the slot (450), when the protecting shroud is inserted into the slot.

According to some embodiments the protecting shroud (510) comprises a seal (530) inside the hollow tube (312) configured to sealingly contact the endoscope when the distal end of the endoscope is inserted into the hollow tube. The protecting shroud (510) further comprises a hermetic screen (518) spanning across the hollow tube and configured to thereby define a closed and sealed space (520) between the hermetic screen and the distal end (316) of the hollow tube. According to some embodiments the protecting shroud further comprises a terrier (522) positioned inside the hollow tube between the seal (530) and the hermetic screen (518) being configured to tear down the hermetic seal upon insertion of the endoscope into the hollow tube.

According to an aspect of some embodiments there is provided a method of preparing an endoscope for an endoscopy procedure. The method comprises providing a protecting shroud (110, 310, 310a, 410, 510) dimensioned to receive therein a distal end (210, 382) of the endoscope, the distal end comprising a view port (220, 390) configured to allow collecting an image of the surrounding of the view port there through. The method further comprises providing a plasma generating field applicator (130, 348, 448) electrically associated with an electric power source. The plasma generating field applicator has a slot (132, 350, 450) configured to receive therein the distal end of the endoscope shrouded within the protecting shroud. The plasma generating field applicator is configured to apply electric power suitable for plasma generation within the protecting shroud (e.g. by the electrodes 330, 340 and 440). The protecting shroud is detachable from the plasma generating field applicator and from the distal end of the endoscope. The method further comprises positioning the distal end of the endoscope shrouded within the protecting shroud in the slot of the plasma generating field applicator, and activating the power source to generate plasma within the protecting shroud, thereby plasma-treating the view port at the distal end of the endoscope.

According to some embodiments, the method further comprises preventing, by the protecting shroud, contamination of the plasma generating field applicator with fluids dispersed on the distal end. According to some embodiments, the plasma generation field applicator comprises a hose (364) and the method further comprises controllably (by closing and opening valve 366) flowing a gas into an inside (322) of the protecting shroud, or pumping the inside of the protecting shroud via the hose.

According to an aspect of some embodiments there is further provided a method of preparing an endoscope (380) for an endoscopy procedure, the endoscope comprising a distal end (382) comprising a view port (390). The view port is made of a dielectric material and is proximal to a metallic segment (384) at the distal end of the endoscope. The method comprises placing the distal end of the endoscope in a closed plasma chamber (e.g. protecting shrouds 310, 310a, 410 or 510, wherein the insertion of the endoscope seals the inside 322 of the protecting shrouds, thereby defining a closed plasma chamber therein). The closed plasma chamber has at least an anode (340, 440) and a cathode (330) wherein the cathode electrically contacts the metallic segment. A line-of-sight between the anode and the cathode is interrupted by a dielectric barrier (344, 444), and the method further comprises applying a plasma-generating electromagnetic field between the anode and the cathode, thereby generating plasma in a DBD mode in a vicinity (322) of the view port. According to some embodiments, the electric barrier (444) electrically isolates the anode (440) from gas in the vicinity (322) of the view port. According to some embodiments of the method, the view port is transparent or alternatively is a mirror. According to some embodiments of the method the view port is made of glass or quartz or plastic.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A method of preparing an endoscope for an endoscopy procedure, the endoscope including a distal end comprising a view port configured to enable collecting an image of the surrounding of the view port there through, the method comprising:
   providing a plasma chamber including an opening and a seal dimensioned and configured to receive the distal end of the endoscope in the opening, the plasma chamber further including at least one electrode electrically associated with a power source and configured to apply in the plasma chamber a plasma generating electromagnetic field;
   inserting the distal end of the endoscope to the plasma chamber through the opening so that the seal and the distal end together seal the opening; and
   supplying electromagnetic power from the power source to the at least one electrode, thereby applying the plasma generating electromagnetic field and generating plasma in the vicinity of the view port.

2. The method of claim 1, further comprising controllably flowing a gas into an inside of the plasma chamber or pumping the inside of the plasma chamber.

3. The method of claim 1 wherein plasma is generated in the plasma chamber in the dielectric barrier discharge mode of operation.

4. The method of claim 1 wherein the plasma chamber includes:
   a protecting shroud having said opening and seal, dimensioned to receive therein the distal end of the endoscope; and
   a plasma generating field applicator, having a slot configured to receive therein the distal end of the endoscope shrouded within the protecting shroud;
   wherein the protecting shroud is detachable from the plasma generating field applicator and the method further comprises preventing, by the protecting shroud, contamination of the distal end by contaminants from the plasma generating field applicator.

5. The method of claim 1, further comprising wetting the view port with a polar liquid following said step of generating plasma.

6. The method of claim 5 wherein said wetting is carried out by dipping the view port in the liquid or by wiping the view port with an article wetted by the liquid or by dispensing a measured amount of the liquid on the view port.

7. The method of claim 5 wherein the liquid is water or an aqueous solution.

8. The method of claim 7 wherein the aqueous solution has a surface tension lower than the surface tension of water.

\* \* \* \* \*